United States Patent
Holle

(10) Patent No.: US 7,922,622 B2
(45) Date of Patent: Apr. 12, 2011

(54) METHOD FOR IMPROVING STRENGTH, FLEXIBILITY, AND COORDINATION

(75) Inventor: Kevin Holle, Chagrin Falls, OH (US)

(73) Assignee: Swiss Therapeutic Training Products, Twinsburg, OH (US)

( * ) Notice: Subject to any disclaimer, the term of this patent is extended or adjusted under 35 U.S.C. 154(b) by 47 days.

(21) Appl. No.: 12/380,716

(22) Filed: Mar. 2, 2009

(65) Prior Publication Data

US 2009/0270228 A1    Oct. 29, 2009

Related U.S. Application Data

(60) Provisional application No. 61/067,507, filed on Feb. 28, 2008.

(51) Int. Cl.
*A63B 71/00* (2006.01)
(52) U.S. Cl. ............ 482/9; 482/1; 482/8; 482/907
(58) Field of Classification Search ............ 482/1–9, 482/900–902, 907; 600/300, 520; 434/247
See application file for complete search history.

(56) References Cited

U.S. PATENT DOCUMENTS

| | | | |
|---|---|---|---|
| 5,269,318 A * | 12/1993 | Nashner | 600/595 |
| 5,554,102 A | 9/1996 | Chiou | |
| 6,063,046 A * | 5/2000 | Allum | 600/595 |
| 6,325,767 B1 | 12/2001 | Wolff et al. | |
| 6,383,150 B1 * | 5/2002 | Stewart et al. | 600/595 |
| 6,389,883 B1 * | 5/2002 | Berme et al. | 73/65.01 |
| 6,527,674 B1 * | 3/2003 | Clem | 482/8 |
| 6,602,172 B1 | 8/2003 | Aigner | |
| 6,637,278 B1 | 10/2003 | Fasanella | |
| 6,644,976 B2 * | 11/2003 | Kullok et al. | 434/236 |
| 7,641,592 B2 * | 1/2010 | Roche | 482/9 |

FOREIGN PATENT DOCUMENTS

| | | |
|---|---|---|
| AU | 2005284158 | 3/2007 |
| CA | 2580706 | 9/2005 |
| DE | 4443756 C1 | 2/1996 |
| DE | 19944456 A1 | 3/2001 |
| DE | 20116277 U1 | 11/2001 |
| MX | MX/A/2007/003231 | 3/2007 |
| WO | PCT/EP2005/054536 | 3/2006 |

\* cited by examiner

*Primary Examiner* — Glenn Richman
(74) *Attorney, Agent, or Firm* — McDonald Hopkins LLC

(57) ABSTRACT

A method of increasing strength, flexibility, and coordination that may establish a person's baseline strength, flexibility, and coordination, while identifying any deficiencies to establish an exercise regimen to address those deficiencies. The method may also include a systematic and consistent warm-up step that will ensure the proper building of strength, flexibility, and coordination while minimizing any potential injury. Lastly, the method may be capable of accurately measuring the progress of the person's training regimen.

17 Claims, 9 Drawing Sheets

METHOD FOR IMPROVING STRENGTH, FLEXIBILITY, AND COORDINATION

CROSS-REFERENCE TO RELATED APPLICATIONS

This application claims benefit from U.S. Provisional Patent Application No. 61/067,507, entitled "Method for Improving Strength, Flexibility, and Coordination," filed on Feb. 28, 2008, which is hereby incorporated in its entirety by reference.

FIELD OF THE INVENTION

The present invention generally relates to a method for increasing strength, flexibility, and coordination, by assessing a person's baseline capabilities, providing a training regimen based on the person's baseline capabilities, and assessing the training regimen results, enhancing the core network development of the human body.

BACKGROUND OF THE INVENTION

Adequate strength, flexibility, and coordination is important for all people to help prevent injuries and to minimize or mitigate, for example, the adverse impact of falls or collisions. It is also important to increase strength, flexibility, and coordination in all people, particularly persons recovering from injury or surgery.

Conventional exercises and exercise programs that attempt to increase strength, flexibility, and coordination, suffer from a number of deficiencies. For example, exercise programs commonly used do not begin with any baseline evaluation or measurement of a person's strength, flexibility, or coordination so that the person does not have an appropriate exercise regimen in the first place. Also, such exercise programs typically rely on the person to prepare for the exercise program by stretching. Often however, the person does not (or is physically unable to) properly stretch, such that the exercises may do more harm than good. In addition, conventional exercises and exercise programs do not address the need to increase coordination, which is an important factor in preventing or mitigating injuries. Further, such exercises and exercise programs do not evaluate the progress of the exercise regimen with respect to strength, flexibility, and coordination.

Accordingly, there is a need in the art for a method of increasing strength, flexibility, and coordination that establishes a person's baseline strength, flexibility, and coordination, while identifying any deficiencies to establish an exercise regimen to address those deficiencies. In addition, there is a need for a method that includes a systematic and consistent warm-up step that will ensure the proper building of strength, flexibility, and coordination while minimizing any potential injury. Lastly, there is a need for a method that is capable of accurately measuring the progress of the person's training regimen. Additional information will be set forth in the description that follows, or may be learned by practicing the teachings set forth in the description.

SUMMARY OF THE INVENTION

A method for improving strength, flexibility and coordination of a person. The method may prepare the person for their initial assessments utilizing a biomechanical stimulation device, assess the strength of the person, and compare the strength assessment results to a database of standards. Based on that comparison, a strengthening exercise regimen is determined and then performed. The method may also assess the coordination of the person and compare the coordination assessment results to a database of standards. Based on that comparison, a coordination exercise regimen is determined and then performed. Lastly, the person is warmed down utilizing a biomechanical stimulation device.

The method may establish a person's baseline strength, flexibility and coordination to establish an exercise regimen to address deficiencies. The method may prepare the person for assessment utilizing a biomechanical stimulation device. After warm up, the method may assess the person's strength and coordination to determine a baseline fitness level and then evaluate the baseline fitness level by reviewing the results of the strength and coordination assessments. After comparing the person's baseline fitness level to a fitness level database, a plurality of strength and coordination exercise regimens for the person are identified based on the baseline fitness level. The plurality of exercise regimens to improve the person's strength, flexibility and coordination are performed and then the person may be warmed down after the exercise regimens.

DESCRIPTION OF THE DRAWINGS

Operation of the preferred embodiments may be better understood by reference to the following detailed description taken in connection with the following illustrations, wherein.

DETAILED DESCRIPTION

While the present invention is described with reference to embodiments described herein, it should be clear that the present invention is not limited to such embodiments. Therefore, the description of the embodiments herein is merely illustrative of the present invention and will not limit the scope of the invention as claimed.

Moreover, while the present method 10 is described in the context of exercise assessments and exercise regimens, it will be appreciated that the method 10 may be used in a variety of different and appropriate contexts, and, as such, any included examples are illustrative in nature and not meant to be restrictive in any way. In addition, the description of the embodiments provided may refer to a specific order of the method 10 steps, however, this should not limit the scope of the embodiments as claimed. Those skilled in the art will understand that the steps of method 10 may be applied in any appropriate order, may be utilized in any number of various circumstances and may be utilized with any appropriate equipment, devices or systems.

Figure 1:
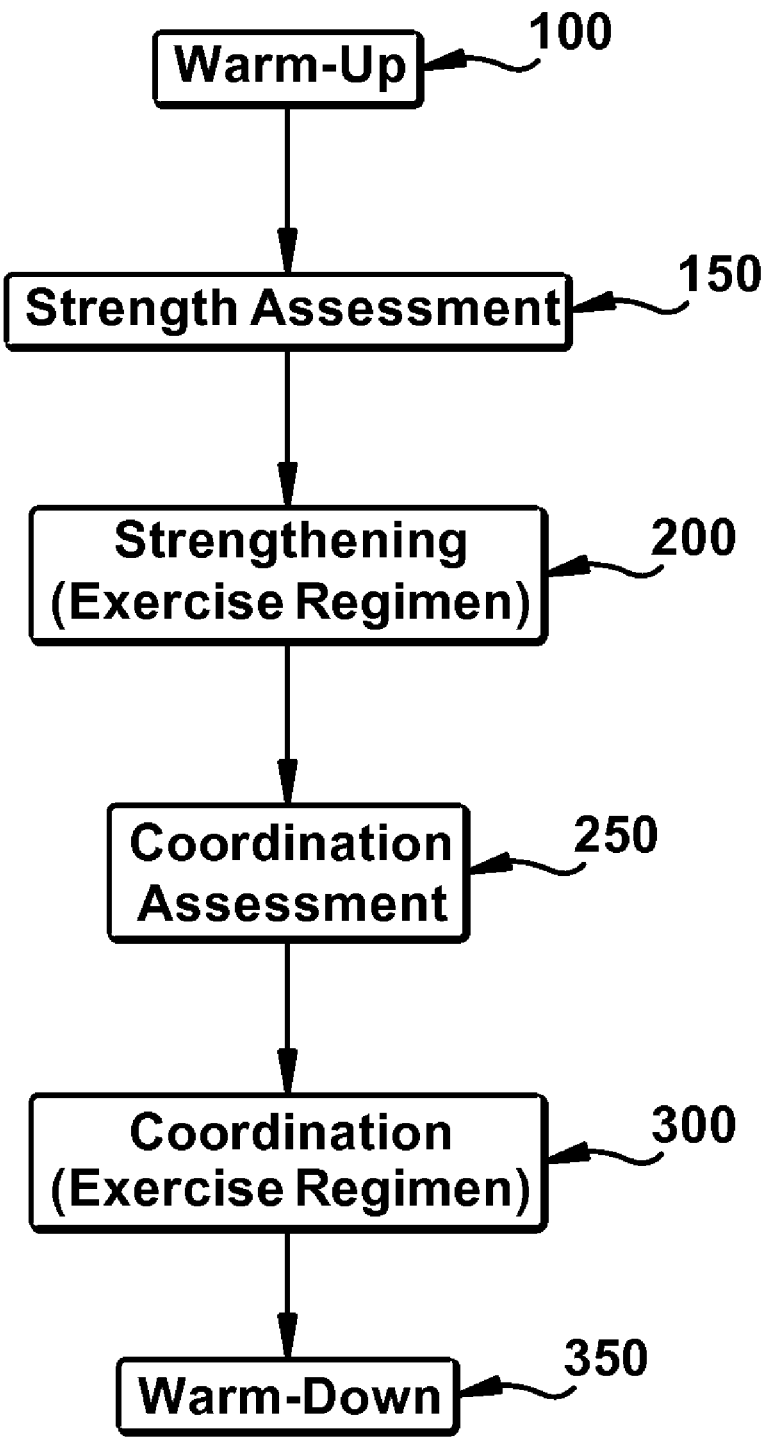
FIG. 1 illustrates a block diagram of an embodiment of a method for improving strength, flexibility, and coordination.

Reference will now be made in detail to the accompanying FIGS. 1-23. As generally described herein and with reference to FIGS. 1-23, the present embodiment provides a method 10. With reference to FIG. 1, the present method 10 may include a warm-up step 100, a strength assessment step 150, a strengthening step 200, a coordination assessment step 250, a coordination step 300, and a warm-down step 350. It is to be understood, that the strength assessment step 150 followed by the strengthening step 200 may be performed in reverse order with the coordination assessment step 250 and the coordination step 300, so that the coordination assessment 250 and coordination regimen 300 occur before the strength assessment 150 and strengthening regimen 200. In addition, the strengthening step 200 and coordination step 300 may also increase flexibility in the person 158.

Accordingly, the present method 10 may be capable of conducting a wide variety of measurements and tests directed to determining the strength, flexibility, and coordination of a person 158. Results from the assessment steps 150, 250 may be compared to a set of standards measured from other persons to provide an appropriate baseline and to determine if a person meets those standards and how far off from those standards that person may be. A targeted exercise regimen 200, 300 may then be provided based on the measurements from the assessment steps 150, 250 to improve any deficiencies or areas of interest to the person 158 in order to increase the strength, flexibility, or coordination of the person. The method 10 may also be capable of such versatility by incorporating several measurement devices to evaluate the progress of the exercise regimen.

Figure 2:
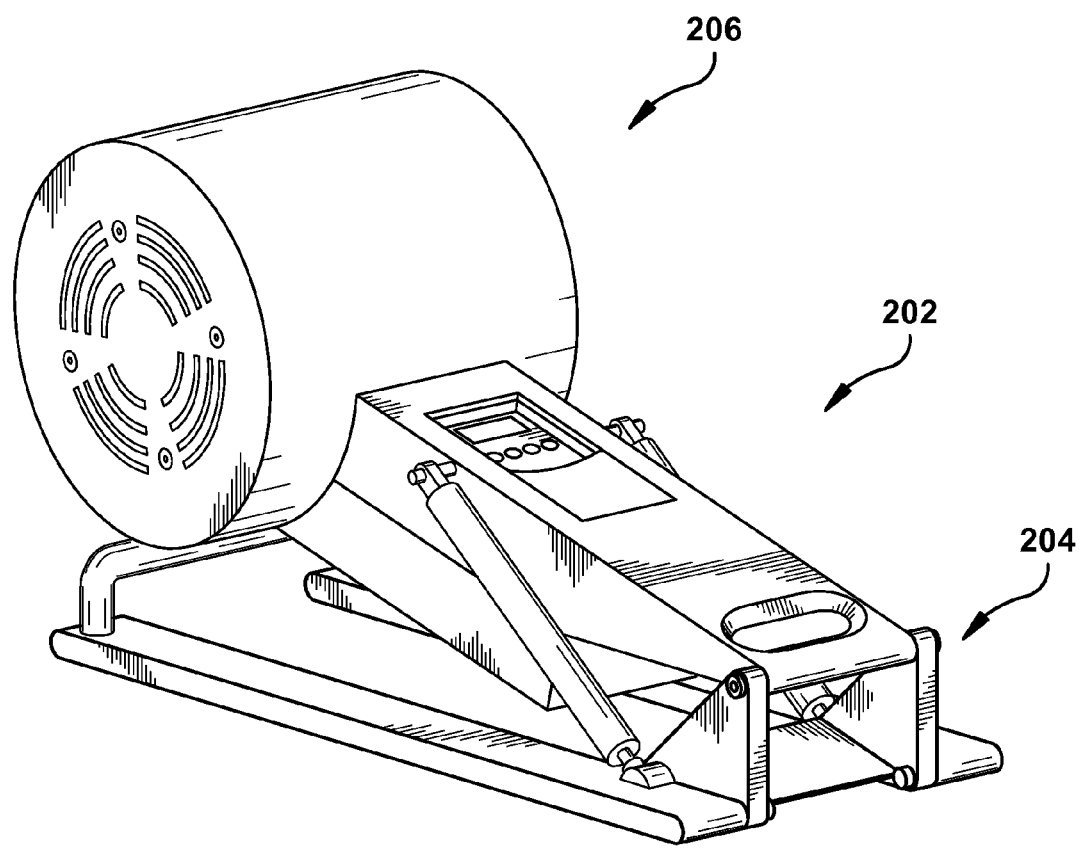
FIG. 2 illustrates a perspective view of preferred embodiment of a warm-up device.
Figure 3:
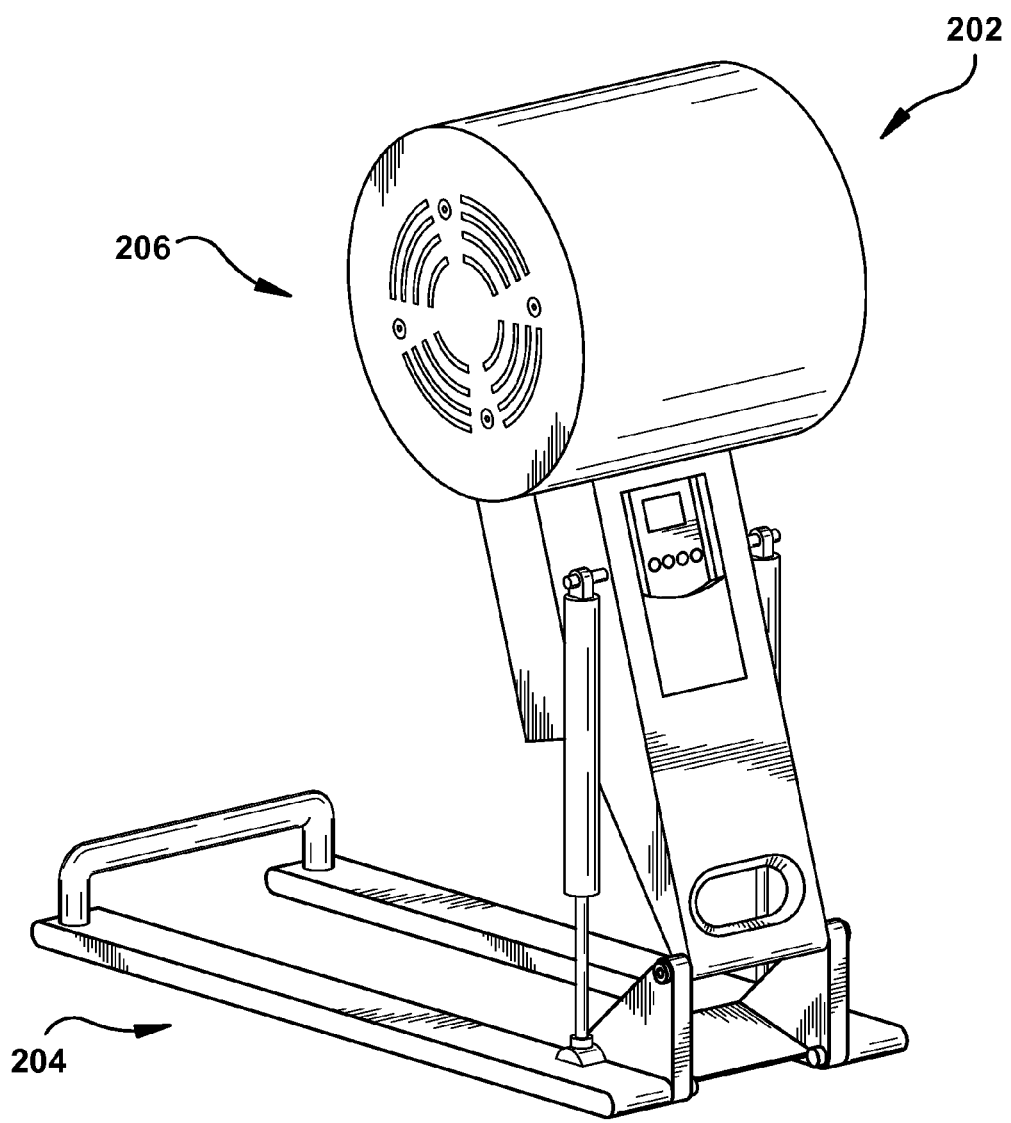
FIG. 3 illustrates a perspective view of an alternative position for the warm-up device of FIG. 2.

With reference to FIGS. 2 and 3, the warm-up step 100 may be performed using a biomechanical stimulation device 202, and as described in U.S. patent application Ser. No. 11/663,254, filed Mar. 19, 2007 (and claiming priority to PCT/EP2005/054536) which is herein incorporated by reference in its entirety. Biomechanical Stimulation (BMS) is based on mechanical influences on the body using vibrations at a respective particular frequency and with a particular amplitude, which may be selected according to the desired application. The vibrations resemble and imitate the natural vibrations of the body and may act on tensed or stretched muscles along the muscle fiber. By influencing the body's own vibration parameters, BMS improves, for example, the circulatory and lymph systems among others.

The BMS device 202 may generate stimulation with a uniform circular or elliptical movement. Thus, the BMS device 202 exerts not only a vertical force, but also a tensile force that acts in a substantially parallel manner, resulting in improved BMS of that part of the body that may be situated on the BMS device 202. The BMS device 202 may include a bottom unit 204 and a stimulation unit 206. The stimulation unit 206 may contain a drive motor that, during operation, provides the elliptical or circular movement. It is to be understood that the BMS device 202 may also include a variety of other appropriate parts or configurations that may be required in order to operate.

In use, the BMS device 202 may be capable of targeting specific areas for stimulation. For example, selected parts of the back, thigh muscles, calves, and arms, among others may be stimulated. The BMS device 202 may stretch and contract the muscles, thereby providing the necessary motion to adequately warm-up the muscles for training 200, 300 or assessment 150, 250. Accordingly, the BMS device 202 may be set on a timer and set at an appropriate frequency to ensure consistency of the warm-up step 100. The warm-up 100 may be especially important for persons, including, but not limited to, unable to perform conventional stretching exercises. In addition, the consistency of the warm-up step 100 may provide the necessary starting point to determine a person's 158 baseline strength and coordination, as well as the progress of the training regimen, as will be discussed below.

The strength assessment step 150, shown in FIG. 1, provides an objective and quantifiable way to test and measure a person's 158 strength or mobility in order to provide for an accurate strength training regimen 200. Mobility and flexibility are the basic requirements for functioning of the arthromusculature system. Movement restrictions, often muscularly conditioned, may cause significant malfunctions and play a role in the emergence of back pain. The assessment step 150 may utilize a force-measuring device and system 152, such as the device and system in U.S. Pat. No. 6,325,767, which is herein incorporated by reference in its entirety.

The strength measurements and tests performed on a person 158 may include, but, are not limited to, the following: (1) measuring the force-exerting ability of the abdominal muscles and the sacrospinal muscle, see FIG. 4, (2) measuring the force-exerting ability of the side and trunk muscles, see FIG. 5, (3) measuring the force-exerting ability of the flexors of the cervical spine and the cervical muscles, see FIG. 6, (4) measuring the force-exerting ability of the of the upper back muscles and the triceps and pectoral muscles, see FIG. 7, and (5) measuring the force-exerting ability of the abductor muscles, see FIG. 8.

FIGS. 4-8 illustrate sample applications of a force-measuring device 152. The force-measuring device 152 may include a variety of pressing elements 154 and force-measuring units 156. The pressing elements 154 may be in the form of cushions, as shown in FIGS. 4-8. The arrangement of the pressing elements 154 and force-measuring units 156 may be arranged in any appropriate manner.

Figure 4:
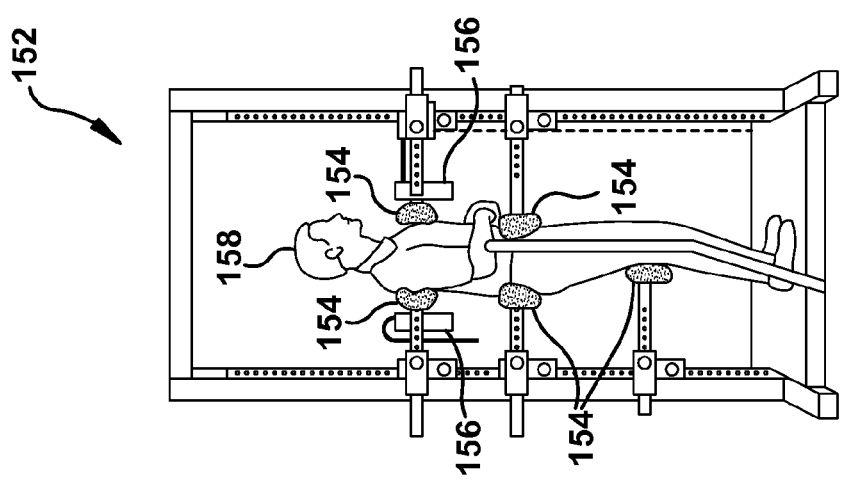

As shown in FIG. 4, the pressing elements 154 may be arranged for measuring the force-exerting ability of the abdominal muscles and the sacrospinal muscle. In the sample embodiment shown in FIG. 4, the hip area of the person 158 may be fixed with the two middle pressing elements 154. The two left and right top pressing elements 154, each of which has a force-measuring unit 156, may lie against the back and chest area of the person 158. Pressing forward on the right force-measuring unit 156 may measure the force-exerting ability of the person's 158 abdominal muscles, while pressing backward on the left force-measuring unit 156 may measure the force-exerting ability of the person's 158 sacrospinal muscle.

Figure 5:
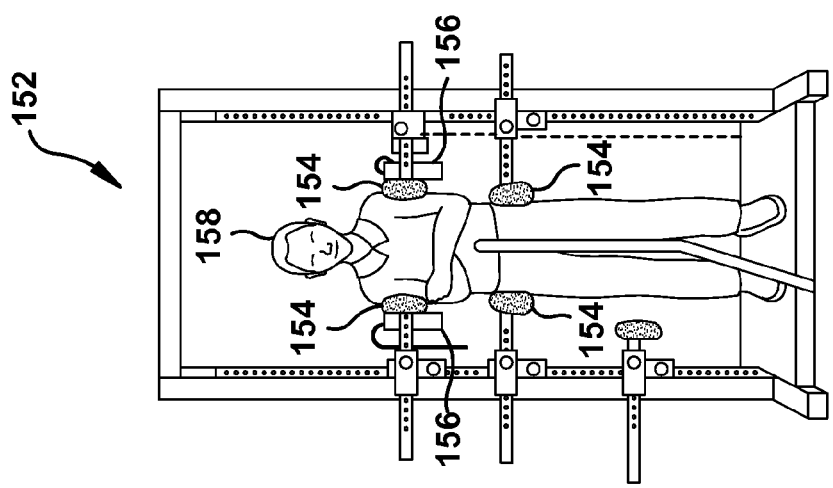

In the design shown in FIG. 5, the hips of the person 158 may again be fixed by the middle pressing elements 154. The two top pressing elements 154, each connected with force-measuring units 156, may lie against the top outside of the upper arms of the person 158. Pressing to the left or right on the respective pressing elements 154 connected with force-measuring units 156 may determine the force-exerting ability of the person's 158 side trunk muscles (lateral flexion).

Figure 6:
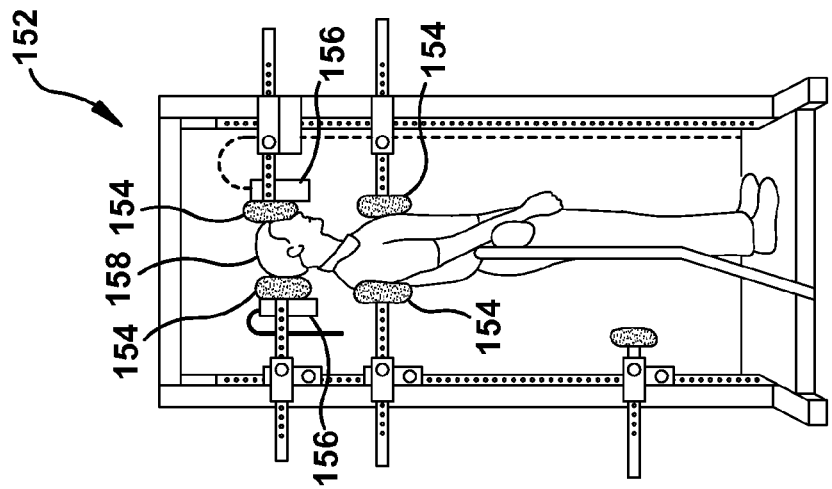
FIGS. 4-8 illustrate different positions for a preferred embodiment of a strength assessment device.

In the arrangement shown in FIG. 6, the person 158 is fixed approximately at chest height by the middle pressing elements 154. The pressing elements 154 connected with the force-measuring units 156 may be located approximately in the area of the back of the person's 158 head and the forehead. Pressing the person's 158 forehead against the pressing element 154 in on the right side of the force-measuring device 152 may determine the force-exerting ability of the flexors of the cervical spine. Pressing the back of the person's 158 head against the pressing element 154 on the left side of the force-measuring device 152 may determine the force-exerting ability of the person's 158 cervical muscles (extensors of the cervical spine).

Figure 7:
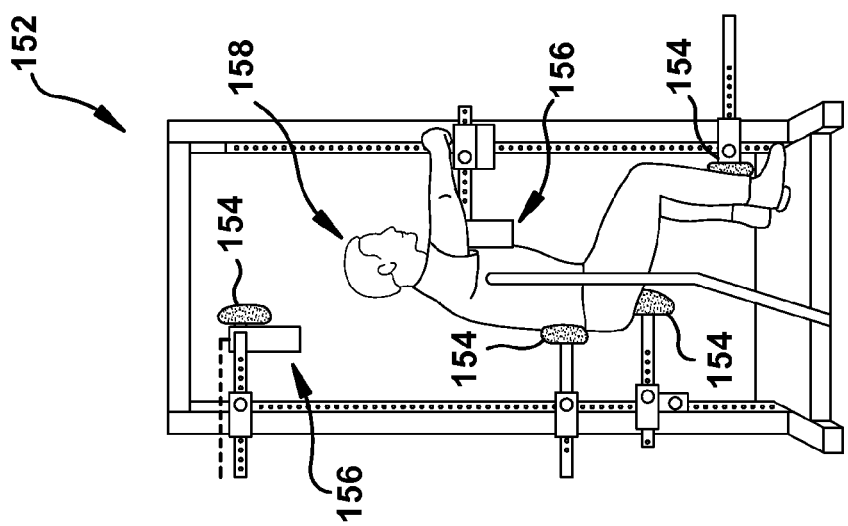

In the arrangement shown in FIG. 7, the lower left pressing element 154 may serve as a sitting surface. The upper left pressing element 154 arranged above it may stabilize the lumbar spine of the person 158. The top right pressing element 154 connected with a force-measuring unit 156 may lie against the chest area of the person 158. The hands of the person 158 may grip the horizontal stay bar. Pulling the person's 158 chest or the upper body against the pressing element 154 in the right part of the force-measuring device may determine the force-exerting ability of the person's 158 upper back muscles.

As an alternative to the arrangement shown in FIG. 7, the upper left pressing element 154 connected with a force-measuring unit 156 may be laid against the area of the shoulder blades of the person 158. In such an arrangement, if the arms are pressed forward against the stay bar, then pressing the person's 158 back against the pressing element 154 may determine the force-exerting ability of the person's 158 triceps and pectoral muscles.

Figure 8:
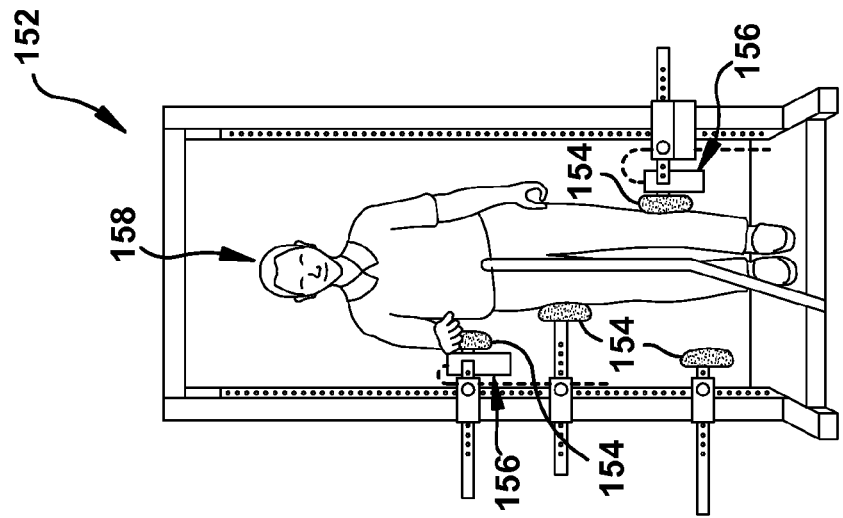

In the arrangement shown in FIG. 8, the left middle-pressing element 154 may lie in the outside area of the right thigh of the person 158. In the approximate area of the opposite knee, the right pressing element 154 connected with a force-measuring unit 156 may lie against it on the outside. Pressing the person's 158 left leg against the cushion set at knee height makes it possible to determine the force-exerting ability of the person's 158 abductors.

In addition to the muscle groups analyzed by the force-measuring device 152 shown in FIGS. 4-8, it is to be understood that other force-exerting abilities may also be tested. Further, the force-measuring device 152 may be incorporated with a multi-functional system for the testing and measurement of the strength of various muscle groups, such as those of the person's 158 back, for example. Therefore, the device 152 may allow a person 158 to attain postural situations, thereby enabling meaningful and accurate measurement of any imbalance or deficiencies of various muscle groups. The force-measuring device 152 may also include a software system that enables a data based documentation of the testing. The person's 158 results may then be compared to stored information regarding the physical characteristics of, for example, particular age groups, sex, height, weight, and numerous other factors in order to assess the person's 158 deficiencies.

In addition, a computer-aided device 160, such as the Spine-Check-Mouse or SpinalMouse® manufactured by idiag AG, may be included in the assessment step 150 to determine the spinal shape and mobility of the person 158. Such a system and device 160 is described in U.S. Pat. No. 6,637,278, which is hereby incorporated by reference in its entirety. It is to be understood that any other appropriate device 160 may be utilized as well.

Figure 9:
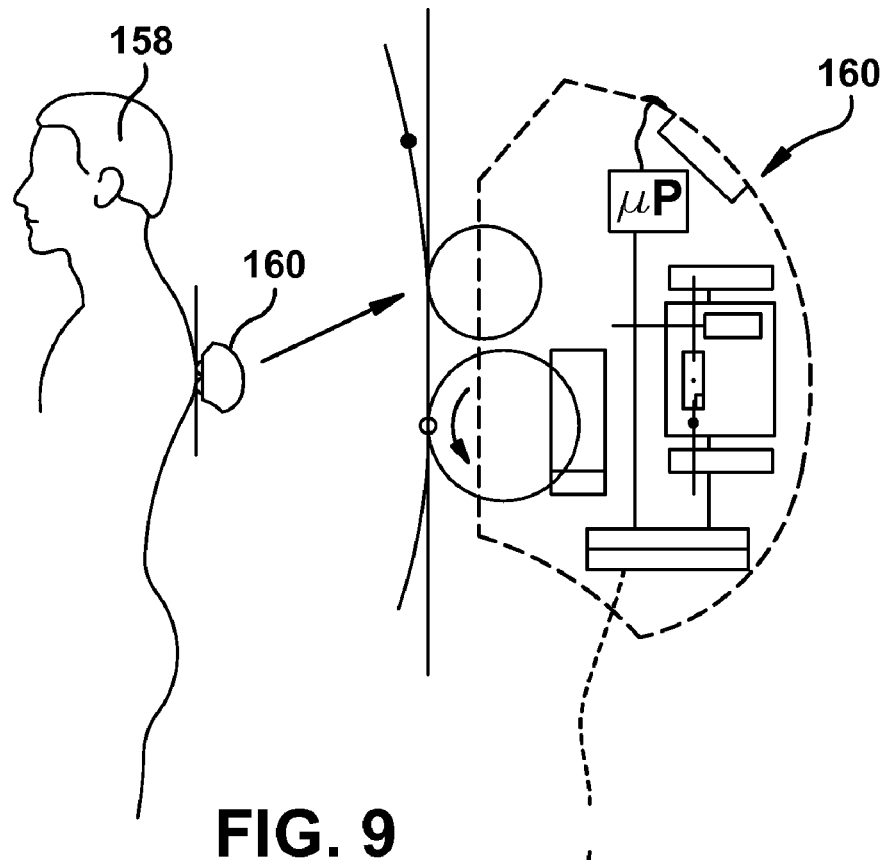
FIG. 9 illustrates a preferred embodiment of an assessment device.
Figure 10:
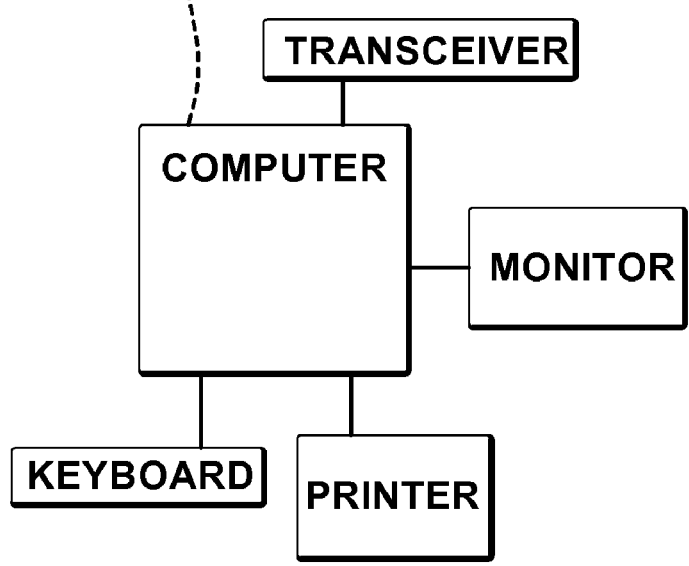
FIG. 10 illustrates a close up view of the assessment device of FIG. 9.
Figure 11:
FIG. 11-18 illustrate preferred embodiments of strength exercise equipment and types of exercises.
Figure 12:
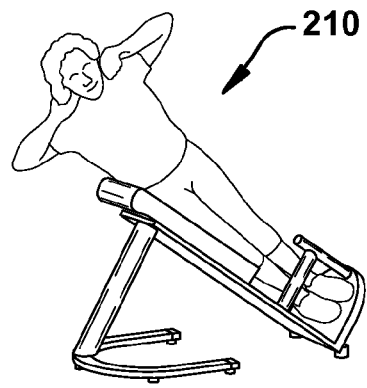
Figure 13:
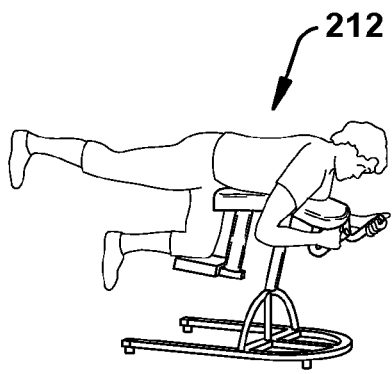
Figure 14:
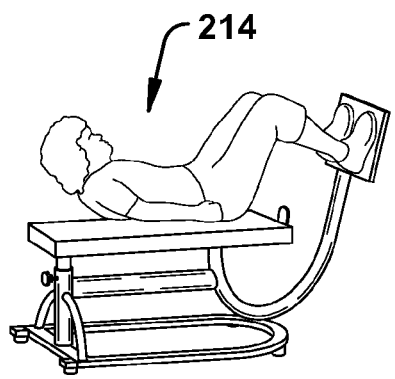
Figure 15:
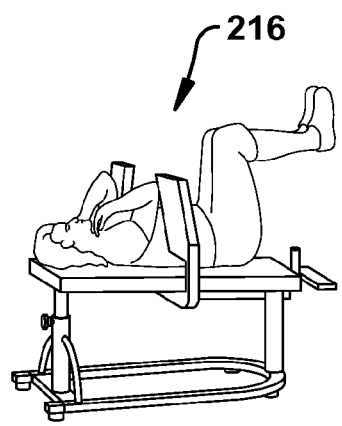
Figure 18:
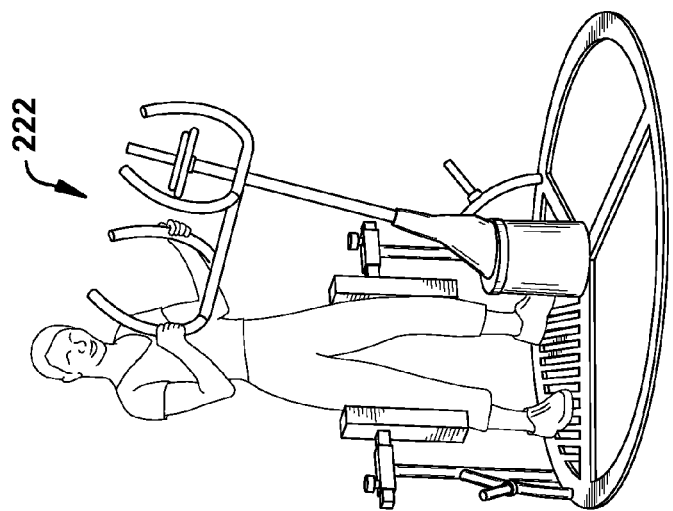
Figure 17:
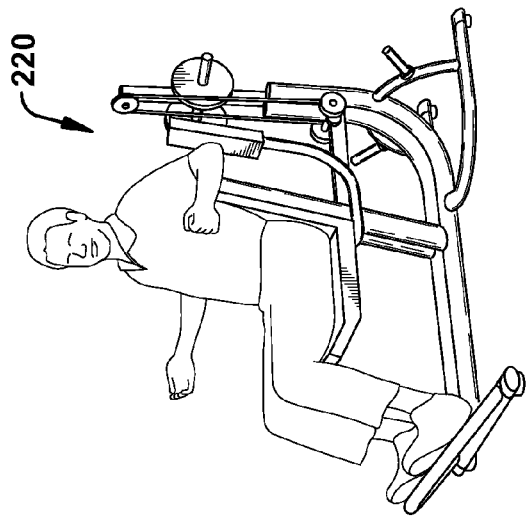
Figure 16:
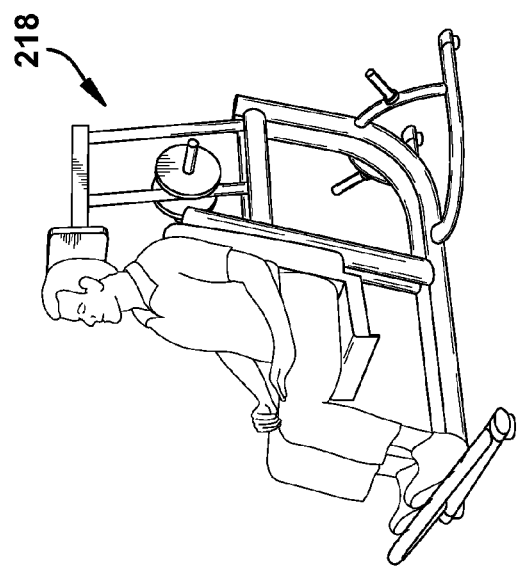

As shown in FIGS. 9 and 10, the device 160 may positioned along the spine of the person 158 to measure the outline of the back and the measurements taken may be sent to a receiving station, such as a computer, to provide examination results in the form of tabulations and graphics. The device 160 may be capable of identifying issues such as functional spinal assessments, scoliosis and other spinal disorders, hypo and hyper mobile vertebral joints or deviations from reference values, cervical, thoracic and lumbar spine information, motion and posture for each vertebral joint, pre- and post-measurements to show impact and success of therapy, load test to identify postural weakness, and other joint measurements such as knees, arms, and elbows.

Based on the information provided by the assessment step 150, a targeted strength exercise regimen may be provided at step 200 to improve any deficiencies identified in the strength assessment 150. As shown in FIGS. 11-18, such strength exercise regimen 200 may include a variety of appropriate exercises. For example and illustrative purposely only, these exercises may utilize various types and forms of equipment, including, but not limited to, equipment manufactured by Dr. WOLFF® Sports & Prevention GmbH. Preferably, the following types of Dr. WOLFF® Sports & Prevention GmbH equipment may be used: lumbal-trainer 208, lateral-trainer 210, gluteus-trainer 212, abdominal-trainer 214, lower abdominal-trainer 216, Neck-trainer 218, posture stabilizer 220, and rotation and stabilization-trainer 222.

With further reference to FIGS. 11-18, the lumbal-trainer 208 may effectively exercise the complete back extensor and gluteal muscles without overloading the back. Strain on the leg flexor may also be reduced. The lateral-trainer 210 may exercise the lateral torso muscles to stabilize the posture. The gluteus-trainer 212 may strengthen the gluteus muscles to aid in preventing incorrect posture of the pelvis. The abdominal-trainer 214 and the lower abdominal-trainer 216 may exercise the stomach muscles without straining the back. The neck trainer 218 may exercise the bending and stretching muscles of the upper back and neck. The posture stabilizer 220 may increase the activity of the posture stabilizing interscapular muscles. The rotation-and-stabilization trainer 222 may exercise the person 158 while in a seated position so not to strain the person 158. It is to be understood that any combination of exercises utilizing the above equipment may be used and that the equipment may be used in any appropriate order. It is also to be understood, that a variety of other additional exercises or equipment may be used alone or in combination with any of the aforementioned illustrative equipment examples.

Figure 19:
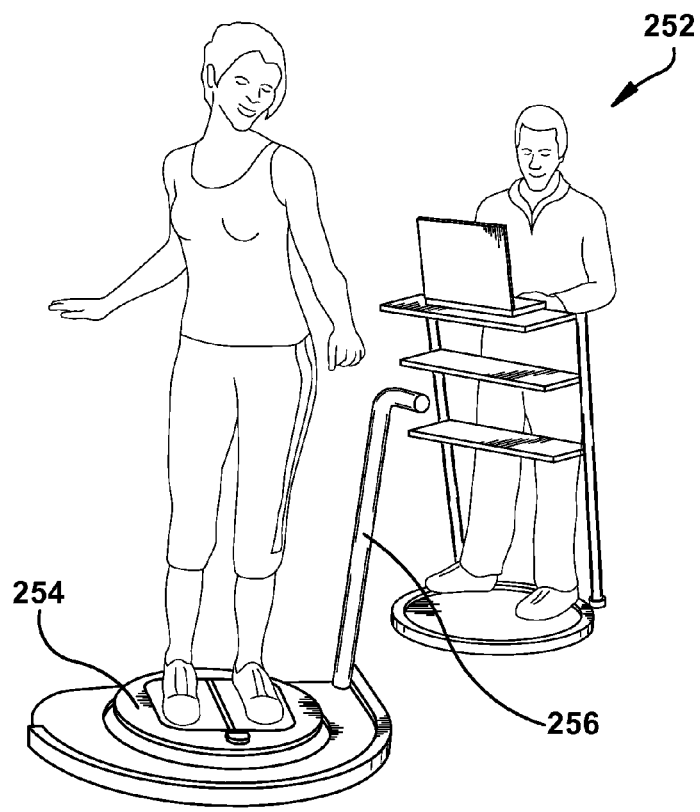
FIG. 19 illustrates a preferred embodiment of a coordination assessment device.
Figure 20:
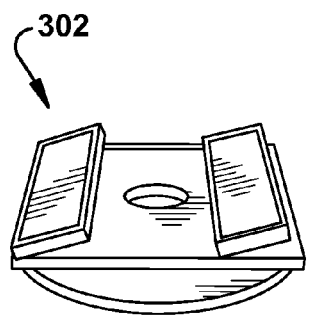
FIGS. 20-23 illustrate preferred embodiments of coordination equipment and exercises.
Figure 21:
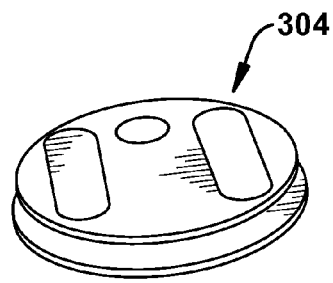
Figure 22:
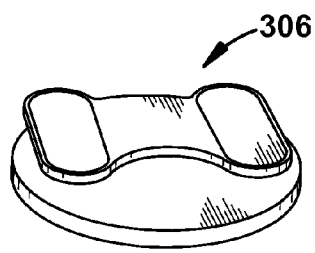
Figure 23:
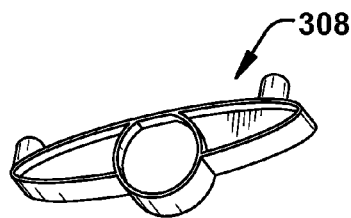

With additional reference to FIG. 1, a coordination assessment 250 of the person's 158 coordination, followed by targeted exercises in coordination step 300 may be provided to improve coordination based at least in part on the weaknesses identified in the assessment step 250. For example and illustrative purposes only, the coordination assessment 250 may be performed with, but not limited to, equipment manufactured by the MFT® S3 Stability Check system 252, as shown in FIG. 19. The MFT® S3 Stability Check system 252 may include a S3 Check measuring Disc 254 and software package 256.

Such a coordination device and system 252 is described in U.S. Pat. No. 6,602,172, which is herein incorporated by reference in its entirety. The stability check system 252 may measure a person's 158 movements to evaluate that person's 158 level of coordination in the coordination assessment step 250. The data that the system 252 measures may give insight into the person's 158 stability, senso-motoric regulation and symmetry in side and forward-backward tilt. The person's 158 results may then be compared to stored information regarding the physical characteristics of, for example, persons of a particular age group, sex, height, weight, and numerous other factors to assess the person's status and any possible deficiencies.

Based on the results of the coordination assessment 250, a coordination exercise training program 300 may then be strategically developed to improve any deficiencies and overall coordination. As shown in FIGS. 20-23, the coordination exercise regimen 300 may include any variety of appropriate exercises, including, but not limited to, the use of stability discs. Preferably, the following types of The MFT® Stability equipment may be used: Sport Disc 302, Fit Disc 304, Trim Disc 306, and Fun Disc 308.

The coordination exercise regimen 300 using the MFT® Stability equipment, may increase body stability, which may support your spine, safeguard your joints and work against strains affecting the boy during movements. Coordination may provide you with more security in everyday life when encountering unexpected situations and aids in protection against injuries. It is to be understood that a variety of other types of appropriate exercises or equipment may be used alone or in combination with any of the aforementioned illustrative examples of exercises and equipment.

Lastly, a warm-down step 350 may also be provided. The warm-down step 350 may be performed with the BMS device 202. Post workout, in the warm-down step 350, the BMS device 202 may provide the necessary pump-like motion to facilitate new blood flow in the targeted areas to decrease the recovery time.

It is to be understood that the assessment steps 150, 250 may also be utilized to measure the progress of the strengthening and coordination steps 200 and 300. For example and illustrative purposes only, a progress assessment may be made at weekly intervals to determine whether to continue the current training regimen or to make modifications. It is to be understood that the exercise regimen steps 200 and 300 may be performed in different orders, and combinations thereof. It is also to be understood that a variety of assessments 150, 250, exercise regimens 200, 300 and intervals are envisioned within the scope of the present invention.

Accordingly, a method 10 is provided for improving strength, flexibility, and coordination. The method 10 includes steps 150, 250 to assess a person's 158 baseline, implement exercise regimens 200, 300 targeted to improve any deficiencies, and document the success or progress of the training regimens 200, 300. Such a method 10 allows for fine-tuning of the training regimens 200, 300 to obtain greater improvement of the core network of the body. In addition, the method 10 includes a warm-up step 100 that is capable of properly warming up a person 158 for exercise or assessment in a consistent manner in order to ensure that any data obtained in the assessment steps 150, 250 is accurate.

The invention has been described above and modifications and alternations will occur to others upon a reading and understanding of this specification. The claims as follows are intended to include all such modifications and alterations insofar as they come within the scope of the claims or the equivalent thereof.

I claim:

1. A method for improving strength, flexibility and coordination of a person, comprising the steps of:
preparing the person for their initial assessments utilizing a biomechanical stimulation device wherein the biomechanical stimulation device stretches and contracts the muscles;
assessing the strength of the person;
comparing the strength assessment results to a database of standards;
determining a strengthening exercise regimen based on coordination assessment results;
performing the strengthening exercise regimen;
assessing the coordination of the person;
comparing the coordination assessment results to a database of standards;
determining a coordination exercise regimen based on the coordination assessment results;
performing the coordination exercise regimen; and
warming down the person utilizing the biomechanical stimulation device.

2. The method of claim 1, wherein the strength assessment step utilizes a force-measuring device.

3. The method of claim 2, wherein the force-measuring device includes a plurality of pressing elements and a plurality of force-measuring units.

4. The method of claim 3, wherein the force-measuring device is incorporated with a multi-functional system for the testing and measurement of the strength of a plurality of muscle groups.

5. The method of claim 4, wherein the force-measuring device includes a software system comparing the person's results to a stored set of standard results.

6. The method of claim 1, wherein the strength assessment performed on the person includes the steps of:
measuring the force-exerting ability of the abdominal muscles and the sacrospinal muscle;
measuring the force-exerting ability of the side and trunk muscles;
measuring the force-exerting ability of the flexors of the cervical spine and the cervical muscles;
measuring the force-exerting ability of the of the upper back muscles and the triceps and pectoral muscle; and
measuring the force-exerting ability of the abductor muscles.

7. The method of claim 6, wherein the strengthening exercise regimen includes the use of a lumbal-trainer, lateral-trainer, gluteus-trainer, abdominal-trainer, lower abdominal-trainer, neck-trainer, posture stabilizer, and rotation and stabilization-trainer.

8. The method of claim 1, wherein the coordination exercise regimen includes stability discs.

9. The method of claim 1, wherein the strength assessment step and the strengthening exercise regimen are performed before the coordination assessment step and the coordination exercise regimen.

10. The method of claim 1, wherein the strength assessment step and the strengthening exercise regimen are performed after the coordination assessment step and the coordination exercise regimen.

11. The method of claim 1, wherein the strength assessment step and the strengthening exercise regimen are preformed concurrently with the coordination assessment step and the coordination exercise regimen.

12. A method for establishing a person's baseline strength, flexibility and coordination to establish an exercise regimen to address deficiencies, comprising the steps of:
preparing the person for assessment utilizing a biomechanical stimulation device wherein the biomechanical stimulation device stretches and contracts the muscles;
assessing the person's strength and coordination to determine a baseline fitness level;
evaluating the baseline fitness level by reviewing the results of the strength and coordination assessments;
comparing the person's baseline fitness level to a fitness level database;
identifying a plurality of strength and coordination exercise regimens for the person based on the baseline fitness level;
performing said plurality of exercise regimens to improve the person's strength, flexibility and coordination; and
warming down the person after the exercise regimens.

13. The method of claim 12, wherein the warm down step utilizes a biomechanical stimulation device.

14. The method of claim 13, wherein the results from the assessment steps are compared to a set of standards measured from other persons to provide an appropriate baseline and to determine how the person compares to those standards.

15. The method of claim 14, wherein the exercise regimens are provided based on the results from the assessment steps to increase the strength, flexibility, or coordination of the person.

16. The method of claim 13, wherein the assessment steps are utilized to measure the progress of the strengthening and coordination steps.

17. The method of claim 13, wherein a progress assessment is made at weekly intervals to determine whether to continue the current exercise regimens or to make modifications.

* * * * *

UNITED STATES PATENT AND TRADEMARK OFFICE
CERTIFICATE OF CORRECTION

PATENT NO.       : 7,922,622 B2
APPLICATION NO.  : 12/380716
DATED            : April 12, 2011
INVENTOR(S)      : Kevin Holle It is certified that error appears in the above-identified patent and that said Letters Patent is hereby corrected as shown below:

Column 7, line 2, delete "boy" and insert --body--

Signed and Sealed this
Nineteenth Day of July, 2011

David J. Kappos
*Director of the United States Patent and Trademark Office*